United States Patent [19]
Stewart et al.

[11] Patent Number: 6,156,499
[45] Date of Patent: Dec. 5, 2000

[54] METHODS FOR DETECTING ANTIBODIES TO HAV 3C PROTEINASE

[75] Inventors: Deneen Stewart, Philadelphia, Pa.;
Tina S. Morris, Rockville, Md.;
Robert H. Purcell, Boyds, Md.;
Suzanne U. Emerson, Bethesda, Md.

[73] Assignee: The United States of America as represented by the Department of Health and Human Services, Washington, D.C.

[21] Appl. No.: 09/142,239

[22] PCT Filed: Mar. 13, 1997

[86] PCT No.: PCT/US97/03428

§ 371 Date: Sep. 3, 1998

§ 102(e) Date: Sep. 3, 1998

[87] PCT Pub. No.: WO97/34136

PCT Pub. Date: Sep. 18, 1997

Related U.S. Application Data

[60] Provisional application No. 60/013,333, Mar. 13, 1996.

[51] Int. Cl.$^7$ ....................................... C12Q 1/70
[52] U.S. Cl. .............. 435/5; 435/7.95; 436/513; 436/518; 436/820
[58] Field of Search ...................... 435/5, 7.95; 436/513, 436/518, 820

[56] References Cited

PUBLICATIONS

Robertson et al., Antibody Response to Nonstructural Proteins of Hepatitis A Virus Following Infection. Journal of Medical Virology 40:76–82, 1993.

Schultheiss et al., Clevage Specificity of Purified Recombinant Hepatitis A Virus 3C Proteinase on Natural Substrates, Journal of Virology 69(3):1727–1733, 1995.

Jokik et al., Eds, Zinsser Microbiology, 20th Ed., 1992 Appleton and Lange, Norwalk, p. 1040.

*Primary Examiner*—Donna Wortman
*Attorney, Agent, or Firm*—Morgan & Finnegan, L.L.P.

[57] ABSTRACT

The present invention discloses methods for detecting antibodies to HAV 3C proteinase. These methods can distinguish an individual with a natural infection from one who has been vaccinated with an inactivated vaccine and are thus of utility in the diagnosis of hepatitis A in situations in which vaccination is widespread.

19 Claims, 17 Drawing Sheets

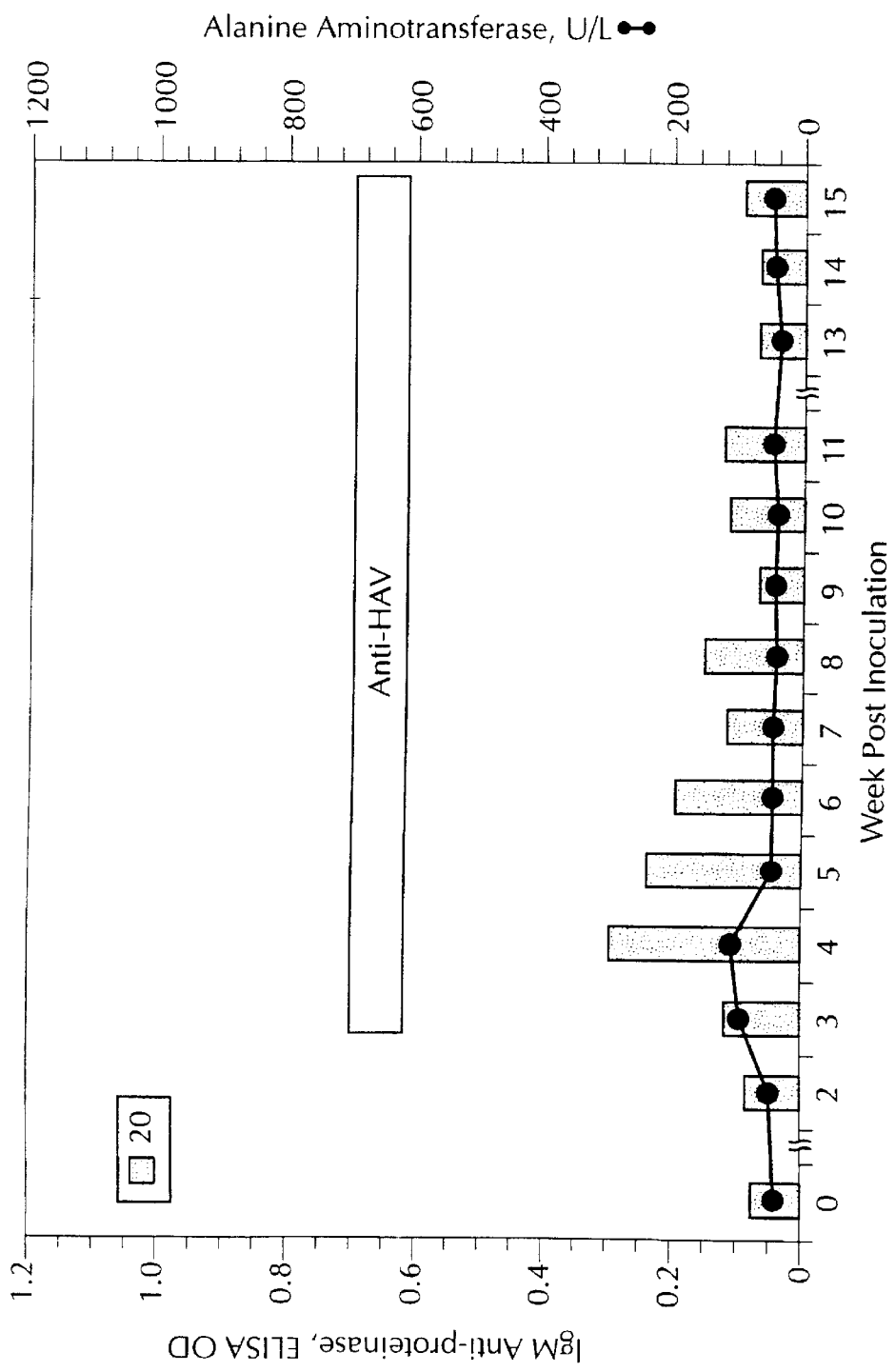

METHODS FOR DETECTING ANTIBODIES TO HAV 3C PROTEINASE

This application is a 371 of PCT/US97/03428, Filed Mar. 13, 1997. This application claims benefit of provisional application 60/013,333, Filed Mar. 13, 1996.

FIELD OF INVENTION

The present invention is in the field of hepatitis A virology. More specifically, the invention relates to methods for detecting antibodies to the hepatitis A virus 3C proteinase.

BACKGROUND OF THE INVENTION

Hepatitis A virus (HAV) is a picornavirus that causes acute liver disease in humans and some lower primates. As with other viruses of the picornavirus family, the genome of HAV contains three regions that encode the proteins of the virus. The structural proteins which form the viral capsid are encoded by the P1 region and the nonstructural proteins, which include viral proteinases, polymerase and other replication proteins are encoded by the P2 and P3 regions.

During a natural infection, the immune system of the infected individual produces antibodies to both the structural and nonstructural proteins (Stapleton et al (1995), *J. Infect. Dis.*, 171 (Suppl. 1): S9–14). By comparison, an inactivated vaccine will induce antibodies to only the structural proteins and not to the nonstructural proteins (Robertson et al. (1993) *J. Med. Virol.*, 40:76–82).

Currently marketed diagnostic assays used to determine HAV exposure detect antibodies to only the structural proteins. Thus, the current testing procedures cannot distinguish an individual with a natural infection from one who has been vaccinated. For diagnostic, safety and epidemiological reasons it is therefore important to develop an immunoassay which is capable of distinguishing whether antibodies were induced by vaccination or by an HAV infection. Previous studies using immunoprecipitation showed the production of antibodies to the entire P2 or P3 regions but not to the 3C proteinase specifically (Jia et al. (1992), *J. Infec Dis.*, 165:273–280; Robertson et al. (1993), *J. Med. Virol.*, 40:76–82).

SUMMARY OF INVENTION

The present invention relates to methods for detecting antibodies specific for the HAV 3C proteinase in biological samples. The methods are useful for diagnosis of infection and disease caused by HAV, for distinguishing a natural infection from vaccination with an inactivated vaccine, and for monitoring the efficacy of preventive agents such as vaccines.

DESCRIPTION OF FIGURES

FIG. 4 shows IgM antibody response to 3C proteinase in a chimpanzee (chimp 1442) inoculated with virulent HAV strain HM-175. The results were plotted as in FIGS. 3A–3F.

DETAILED DESCRIPTION OF INVENTION

Figure 1A:
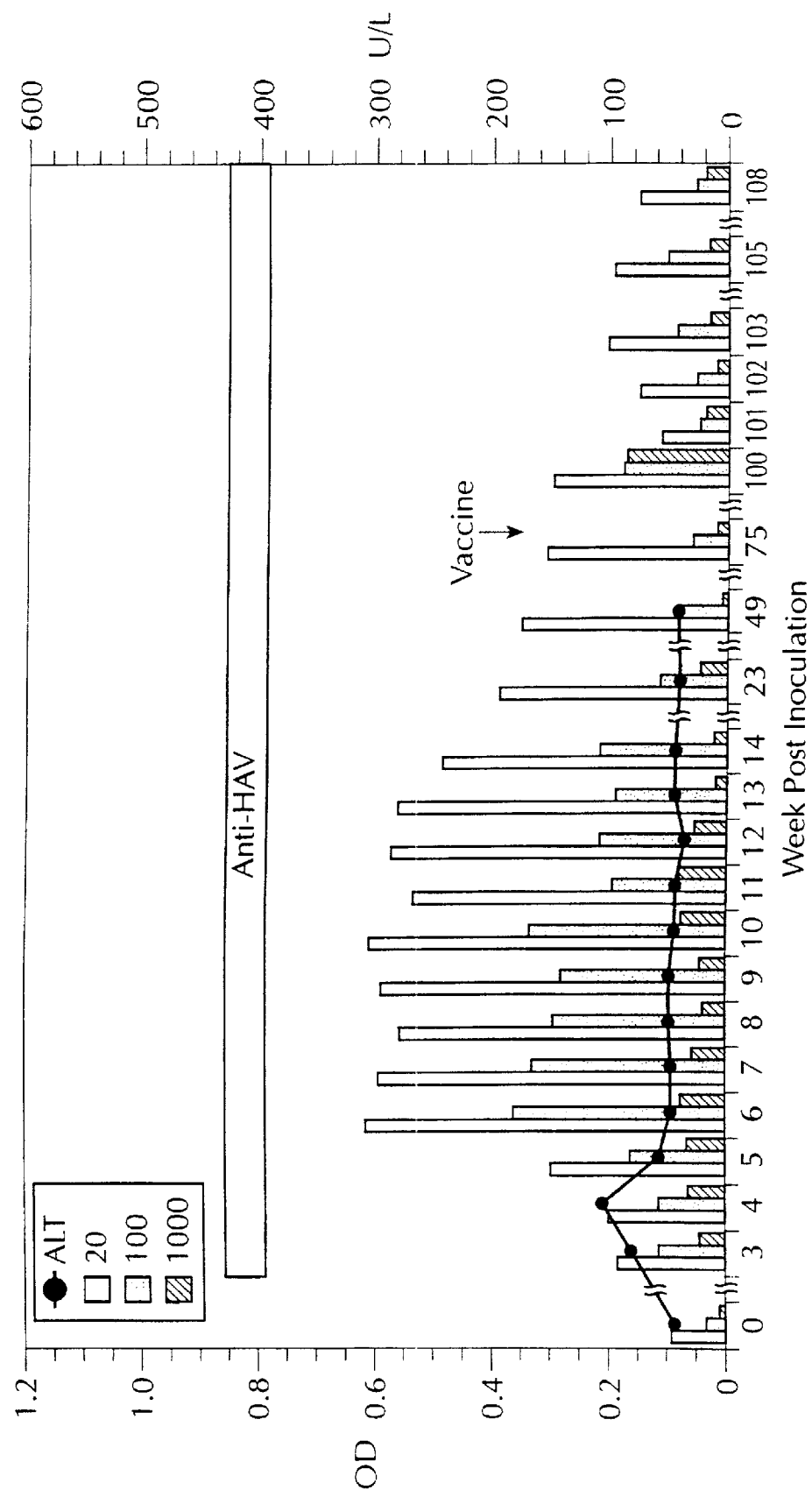
FIGS. 1A–1F show anti-3C proteinase antibody response compared to seroconversion to the structural proteins (anti-HAV) and to alanine aminotransferase (ALT) levels in chimpanzees with hepatitis following inoculation with wild-type virus HM-175 (FIG. 1A) or SD-11 (FIGS. 1B and 1C), or in chimpanzees with an infection modified by injection of immune serum globulin (ISG) prior to inoculation with wild-type HM-175 (FIGS. 1D–1F). ALT levels are indicated as units/liter (U/L) on the right-hand vertical axis of FIGS. 1A–1F; OD levels for the anti-3C proteinase ELISA obtained using 1:20, 1:100 or 1:1000 dilutions of sera are indicated in the Figures as bars marked 20, 100 and 1000, respectively; and the horizontal bar labelled anti-HAV in each of FIGS. 1A–1F represents samples which were seropositive for HAV structural proteins (value of N/S>2.0 for antibodies to HAV structural proteins).

The present invention relates to methods for detecting antibodies to HAV 3C proteinase in a biological sample. Biological samples appropriate for the detection assays of the invention include, but are not limited to, whole blood, serum, plasma and saliva.

In one embodiment, the methods of detection are immunoassays having as an antigen, recombinantly expressed HAV 3C proteinase. Immunoassays of the present invention may be a radioimmunoassay, Western blot assay, immunofluorescent assay, enzyme immunoassay, chemiluminescent assay; immunohistochemical assay, ELISA and the like (Principles and Practice of Immunoassay (1991) eds., Price, Christopher P. and Newman, David J., Stockton Press, NY, N.Y.; and Current Protocols In Molecular Biology, eds., Ausubel, F. M. et al. (1994) John Wiley & Sons, NY, N.Y.). Such assays may be direct, indirect, competitive or noncompetitive.

In a preferred embodiment, the immunoassay is an ELISA in which test serum is reacted with a solid phase reagent having surface-bound recombinant HAV 3C proteinase as an antigen as described in the Examples section herein. In one embodiment, after reaction of the antigen with anti-HAV 3C proteinase antibodies, the antigen-antibody complex may be detected by reaction with a secondary antibody such as labelled anti-human antibody. The label may be an enzyme which is detected by incubating the solid support in the presence of a suitable fluorimetric or colorimetric reagent. Other detectable labels such as radiolabels may also be used.

In a second embodiment, the methods of detection are functional assays which measure the ability of antibodies in a biological sample to inhibit HAV 3C proteinase activity. In the functional assays of the present invention, HAV 3C proteinase may be preincubated with antibodies/sera and then HAV 3C proteinase activity may be measured by a number of methods, including, but not limited to, detecting the release of amino groups during proteolysis of polypeptide or peptide substrates by recombinant 3C proteinase using calorimetric or fluorimetric reagents such as trinitrobenzenesulfonate (TNBS) (Malcolm et al. (1992) *Biochemistry* 31:3358–3363); via incubation of recombinant 3C proteinase with radiolabelled in vitro translation products which are 3C proteinase substrates (Schultheiss et al. (1995) *J. Virol.*, 69:1727–1733); or via separation by reverse phase HPLC of peptide substrates cleaved by recombinant 3C proteinase. (Schultheiss et al., (1995) *J. Virol.*, 69:1727–1733). Since the 2C/3A (amino acids 1422/1423 of the HAV polyprotein), 2A/2B (amino acids 836/837 of the HAV polyprotein) and 2B/2C (amino acids 1087/1088 of the HAV polyprotein) junctions are efficiently cleaved by 3C proteinase, suitable substrates for 3C proteinase in the functional assays of the invention include recombinantly produced polyproteins or peptides, or synthetic peptides, which span these cleavage sites. Since the genome organization and the nucleotide and amino acid sequences of HAV are known (Cohen et al (1987), *J. Virol.*, 61:50–59), the design of such polypeptides or peptides is well within the ordinary skill of the art.

Preferred 3C substrates in the functional assays of the invention are synthetic peptides spanning the 2B/2C cleavage sites. Examples of such a peptide is one having the sequence ELRTQFS-NH$_2$ (SEQ ID NO:1) (Malcolm et al., (1992) *Biochemistry* 31:3358–3363).

The recombinant 3C proteinase utilized in the immunoassays and functional assays of the invention may be recombinantly expressed in prokaryotic cells such as *E. coli* or in eukaryotic cells using vectors and methods known to those of ordinary skill in the art. In a preferred embodiment, recombinant 3C proteinase may be expressed in *E. coli* as described in Jia et al., ((1991) *J. Virol.*, 65:2595–2600), Gauss-Muller et al., ((1991) *Virology*, 182:861–864), Malcolm et al., (1992) *Biochemistry* 31:3358–3363); and Schultheiss et al., (1995) *J. Virol.*, 69:1727–1733). In a more preferred embodiment, the recombinant 3C proteinase is expressed in *E. coli* using the pET-3CD* plasmid of Schultheiss et al., *J. Virol.*, 69:1727–1733). Of course, one of ordinary skill in the art would readily understand that the 3C proteinase utilized in the methods of detection of the present invention could be obtained by methods other than recombinant expression such as via chemical synthesis.

In one embodiment, the recombinantly expressed HAV 3C proteinase can be obtained as a crude lysate or it can be purified by standard protein purification procedures known in the art which may include differential precipitation, molecular sieve chromatography, ion-exchange chromatography, isoelectric focusing, gel electrophoresis, affinity, and immunoaffinity chromatography and the like. In the case of immunoaffinity chromatography, the recombinant protein may be purified by passage through a column containing a resin which has bound thereto antibodies specific for the 3C proteinase.

In a preferred embodiment, the recombinant HAV 3C proteinase used in the methods of the invention is partially purified or purified. An example of a preferred protocol for the purification of recombinantly expressed HAV 3C proteinase is provided in the Materials and Methods section described herein for the "further purified 3C proteinase".

Since the methods of the present invention detect antibodies to the 3C proteinase in serum of infected individuals but not in serum of vaccinated individuals, the methods are useful in distinguishing infected individuals from vaccinated individuals. In addition, since the presence of antibodies to the 3C proteinase is indicative of viral replication, the methods of the invention may be useful in monitoring the efficacy of preventive agents such as vaccines.

The present invention provides kits useful for the detection of anti-3C proteinase antibodies in a biological sample. Such kits may contain the recombinant HAV 3C proteinase alone, or in combination with other reagents such as other non-structural proteins like the 3D polymerase, or with secondary antibodies for use in immunoassays, or with synthetic peptide substrates for use in functional assays.

All articles or patents mentioned herein are hereby incorporated by reference. The following examples illustrate various aspects of the invention but are in no way intended to limit the scope thereof.

EXAMPLES

Materials and Methods

Expression and purification of 3C proteinase

The construction of the plasmid pET-3CD* has been described previously (Schultheiss, T. et al., (1995) *J Virol.* 69:1727–1733)). pET-3CD*, which contains the entire 3C gene from the HAS-15 strain of HAV and the 70 N-terminal amino acids of 3D was transformed into competent BL21 cells. After the transformation, individual colonies were selected and bacteria were cultured in N-Z amine (NZA) medium containing 50 ug/ml of ampicillin. Once the OD$_{595}$ reached 0.5, isopropyl thiogalactopyranoside (IPTG) was added to a final concentration of 0.5 mM. Thirty minutes after the addition of IPTG, the antibiotic rifampicin (150 ug/ml) was added to reduce bacterial protein production. Three hours after induction with IPTG, the bacteria were harvested by centrifugation and resuspended in a lysis buffer (50 mM Tris-HCl pH 8.5, 2.5 mM EDTA, 2 mM DTT, 80 ug/ml lysozyme). The suspension was then alternately frozen and thawed 5 times to lyse the bacteria. The lysate was clarified by centrifugation and the supernatant was incubated overnight at 4° C. with DEAE-Sephadex A-25 (Pharmacia, Piscataway, N.J.) that was equilibrated in buffer (50 mM Tris-HCl pH 8.5, 2.5 mM EDTA, 2 mM DTT). The supernatant from the Sephadex mixture was removed from the resin using a 0.2 μm filter. To isolate the proteinase, the supernatant was chromatographed on a CM-Sepharose (Pharmacia) column and eluted with a linear salt (NaCl) gradient from 0 to 1M in the above buffer (50 mM Tris-HCl pH 8.5, 2.5 mM EDTA, 2 mM DTT). Fractions were analyzed for 3C proteinase content by Western blot using antibodies to the recombinantly expressed 3C proteinase. The 3C proteinase-containing fractions were pooled and then concentrated in a Centricon 10 microconcentrator. The purified 3C proteinase obtained at this step (referred to herein as "the purified 3C proteinase") was used as the antigen in the ELISAs described in Examples 1 and 2.

For use in the ELISAs described in Examples 3 and 4, the 3C proteinase was further purified (referred to herein as "the further purified 3C proteinase") as follows: The 3C proteinase concentrated in the Centricon 10 microconcentrator was chromatographed on a column of Sepharose 300SW (Pharmacia) and eluted off the column in Tris (25 mM) buffered saline (TBS) pH 7.5. A final purification step involved binding the proteinase on a column of hydroxyapatite and eluting it with a linear gradient of 10 to 400 mM $KH_2PO_4$.

The activity of the purified or further purified 3C proteinase was determined by cleavage of in vitro generated radiolabelled polyprotein substrate as described in Schultheiss et al, ((1995) *J. Virol.,* 69:1727–1733) and the protein concentration of the 3C proteinase was determined by commercially available assay (BioRad). The proteinase had a MW of 26,000 kDa (the MW of the 3C proteinase) since the 70 N-terminal amino acids of the 3D protein were cleaved from the 3CD* expression product by the 3C proteinase. By silver staining, the purified 3C proteinase was about 95% pure (data not shown).

Anti-3C Proteinase ELISA

"Purified 3C proteinase" or "further purified 3C proteinase" was diluted in 0.05 M carbonate buffer (pH 9.6) to a final concentration of 0.1 ug/100 ul and placed in 96 well microtiter plates and incubated overnight at 4° C. The wells were washed 4 times with phosphate buffered saline (PBS)/1% Tween 20 and then incubated with blocking buffer (PBS with 10% fetal calf serum (FCS) and 1% gelatin) for 1 hour at 37° C. After removal of the blocking buffer, the wells were washed again four times with PBS/1% Tween 20. Serum from chimpanzees or tamarins, diluted 1:20, 1:100 or 1:1000 (1:50, 1:100 or 1:1000 for tamarin 682—see FIG. 2A) in blocking buffer, was added to the microtiter plate and incubated for 1 hour at 37° C. After this incubation the microtiter plate was washed 4 times with PBS/1% Tween 20. Anti-human IgG and IgM labeled with horseradish peroxidase (Organon Teknika Cappel, West Chester, Pa.) was used to detect antibodies to the HAV proteinase in chimpanzees while anti-new world monkey IgG (Tsarev et al. (1993) *J. Infect. Dis.,* 168:369–378) (labelled with horseradish peroxidase by Accurate Chemical and Scientific Co., Westbury, N.Y.) was required for the tamarins. The final color development was produced by the addition of 2,2'-azino di-ethylbenzothiazolinesulfonic acid (ABTS) and incubation of the microtiter plate for 20 minutes at room temperature. Samples with an OD value at 405 nm of >0.2 in the ELISA were considered positive. This cut-off value represents 2 standard deviations above the mean value of known negative samples.

Serum samples

Serum samples were collected from chimpanzees (*Pan troglodytes*) and tamarins (*Saguinus mystax*) that were treated as follows.

Chimpanzees 1442 and 1300 were inoculated intravenously with 1,000 chimp infectious doses of wild-type HM-175 (Daemer, R. J. et al. (1981) *Infection and Immunity,* 32:388–393) while chimpanzees 1373 and 1451 were infected orally with 1 to 10 oral infectious doses of the wild-type SD-11 strain (Dienstag, J. L. et al. (1975) *Annals of Internal Medicine,* 83:647–650).

Chimpanzee 1374 was administered 4 ml of immune serum globulin (ISG) intravenously and Chimpanzees 1396 and 1420 were each given 0.3 ml ISG intramuscularly. All 3 chimpanzees were then challenged two days post-inoculation with 1000 chimp infectious doses (CID) of wild type HM-175 intravenously.

Chimpanzees 1332 and 1380 were vaccinated intramuscularly with 360 ELISA units of an inactivated HAV vaccine (HAVRIX, a killed HAV vaccine commercially available from SmithKline Beecham).

Chimpanzees 1309 and 1333 were vaccinated by intravenous inoculation with 1.0 ml of a $10^{-3}$ dilution of a live attenuated strain of HM-175 (Purcell, R. H. et al. (1992) *Vaccine* (Suppl. 1) 10:5148–152) and challenged intravenously with 1.0 ml of $10^3$ chimpanzee infectious doses (CID) of wild-type HM-175 35 weeks post-vaccination.

Chimpanzees 88A02 and 88A04 were inoculated intravenously with a 10% liver suspension containing live AGM-27, a simian strain of HAV (Emerson, S. V. et al. (1996) *J. Infect. Dis.* 133:592–597); they were later sequentially challenged intravenously with 1000 CID of the HM-175 strain and with a 102-2 dilution of a stool pool of the SD-11 strain.

Tamarin 682 was inoculated intrahepatically with a 100 μl transcription reaction of HAV DNA clone 84 which encodes a virus with a wild-type phenotype (Emerson et al. (1992) *J. Virol.,* 66:6649–6654) while tamarin 683 was inoculated intravenously with $10^5$ tissue culture infectious doses of an attenuated strain of HM-175, pHAV/7 (Cohen et al. (1987) *J. Virol.* 61:3035–3039).

Serum samples from inoculated chimpanzees and tamarins were analyzed for alanine amino transferase (ALT) and isocitrate dehydrogenase (ICD) by commercial methodology (Metpath, Rockville, Md.). Levels of ALT or ICD greater than or equal to twice the mean pre-challenge value were indicative of biochemical evidence of hepatitis. Primates were housed under BL-2 biohazard containment. The housing, maintenance and care of the animals met or exceeded all requirements for primate husbandry.

Antibodies to the structural proteins of HAV were identified with a commercially available competitive binding radioimmunoassay (RIA) or enzyme immunoassay (EIA) assay (Abbott Laboratories, Abbott Park, Ill., cut off value for both assays=N/S>2.0 where N/S represents Normal positive control/test Sample).

Example 1

Detection of anti-3C proteinase antibodies in chimpanzees

A chimpanzee (1442) infected with the wild-type HAV strain HM-175 exhibited seroconversion to the structural proteins and peak ALT levels at weeks three and four postinoculation respectively. IgG antibodies to the 3C proteinase appeared later at week five as shown in FIG. 1A. The antibodies to the nonstructural 3C protein were detected through week 100 post-infection, after which they decreased below the level of detection. Anti-3C antibodies were not boosted following inoculation intramuscularly with 360 ELISA units of inactivated HAV-HAVRIX vaccine (SmithKline Beecham) at week 75; however there was a significant boost in the antibodies to the structural proteins (data not shown).

Figure 1B:
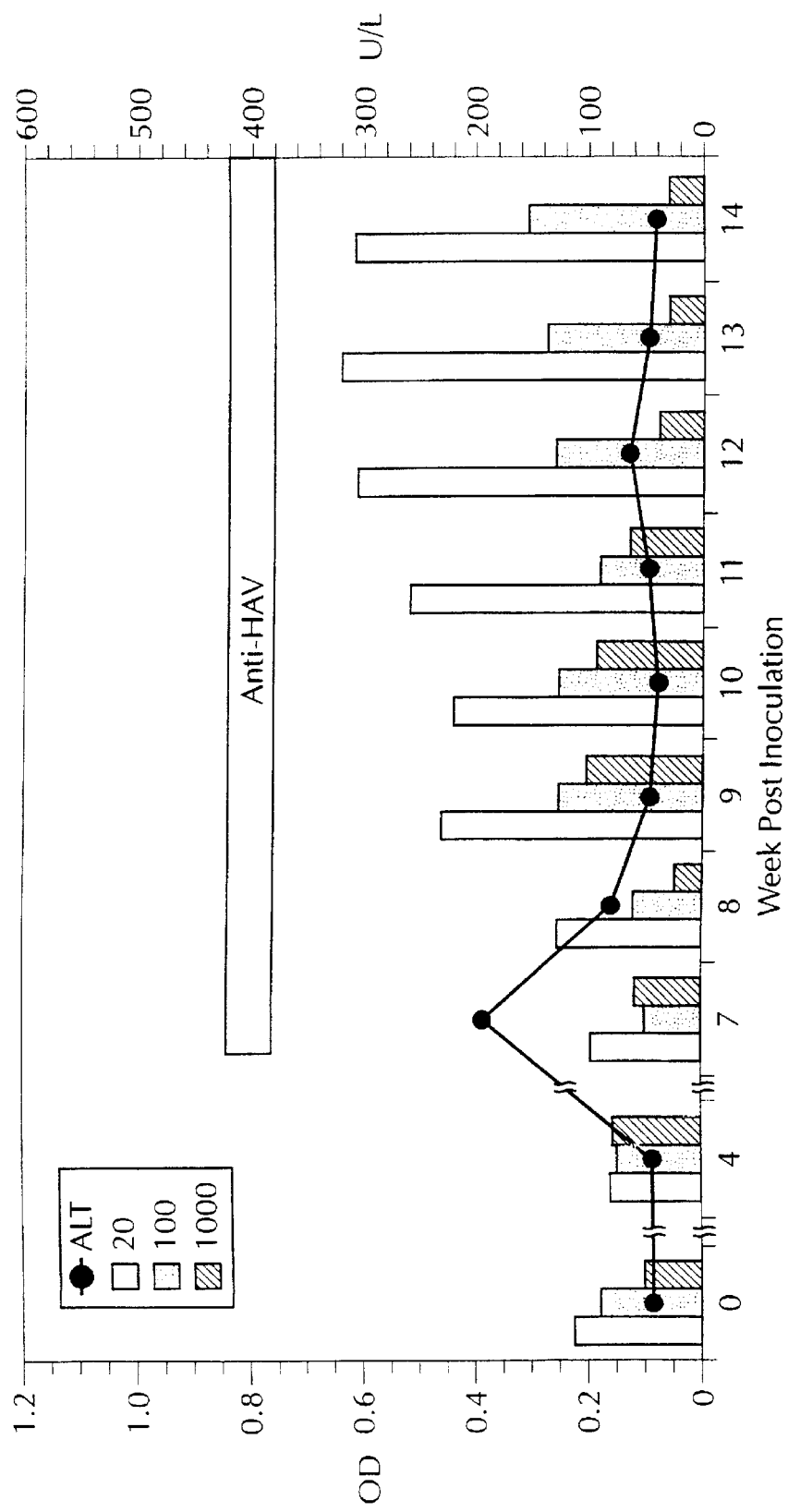
Figure 1C:
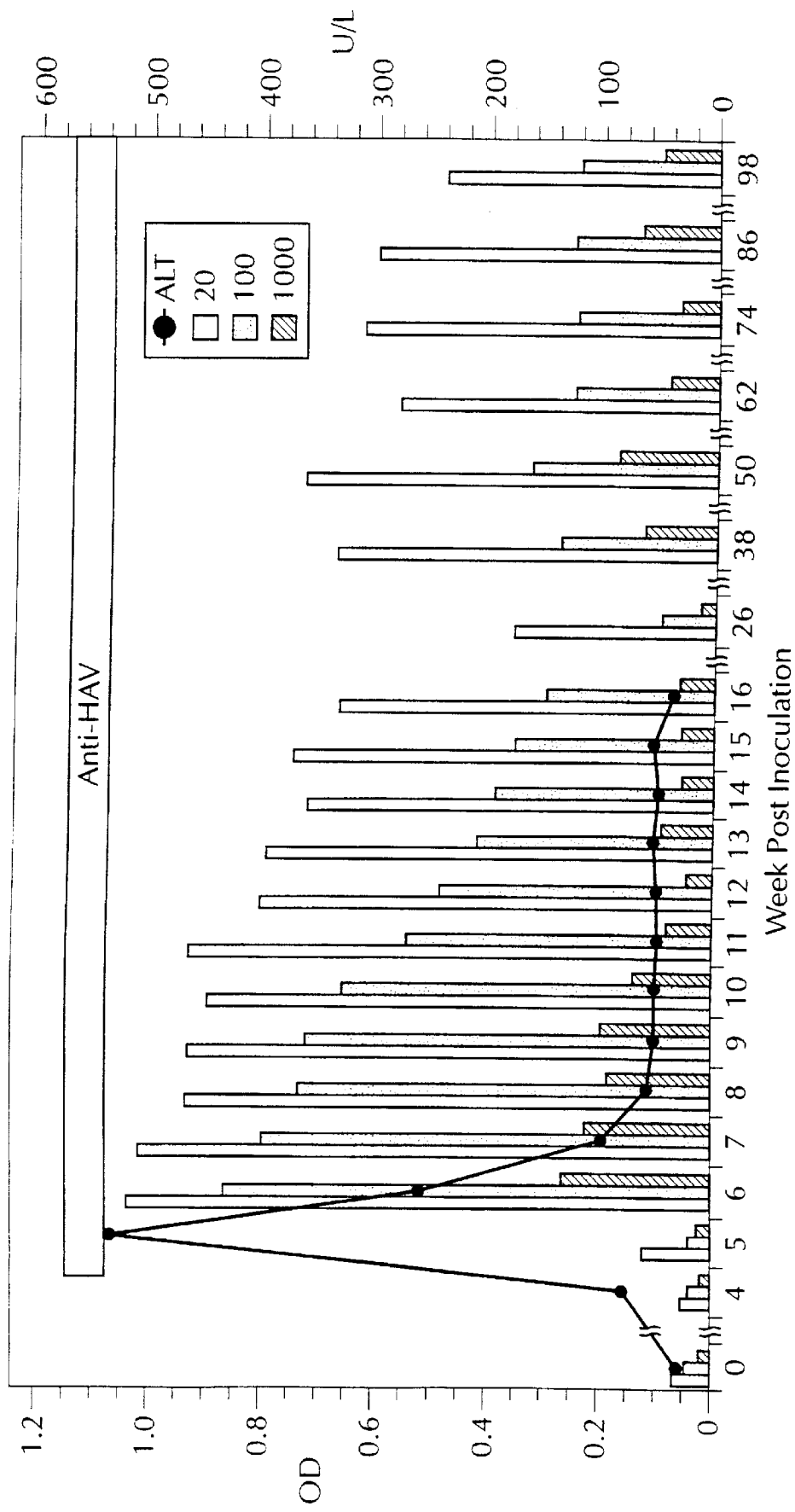

To determine if the ELISA could detect anti-3C antibodies in chimpanzees infected with an HAV strain other than HM-175, serum from animals infected with the HAV strain SD-11 was analyzed. As shown in FIGS. 1B and 1C, the ELISA was able to detect antibodies to the proteinase in the SD-11 infected chimpanzees 1373 and 1451. As with the HM-175 infected chimpanzee, the antibodies to the proteinase were first detected after seroconversion to the structural proteins had occurred and close to the time of peak ALT elevation. These results demonstrate the versatility of the 3C proteinase ELISA since serum generated by chimpanzees that were infected with two different HAV strains, either HM-175 or SD-11, contained anti-proteinase antibodies which reacted with the recombinantly expressed HAS-15 3C proteinase.

Figure 1D:
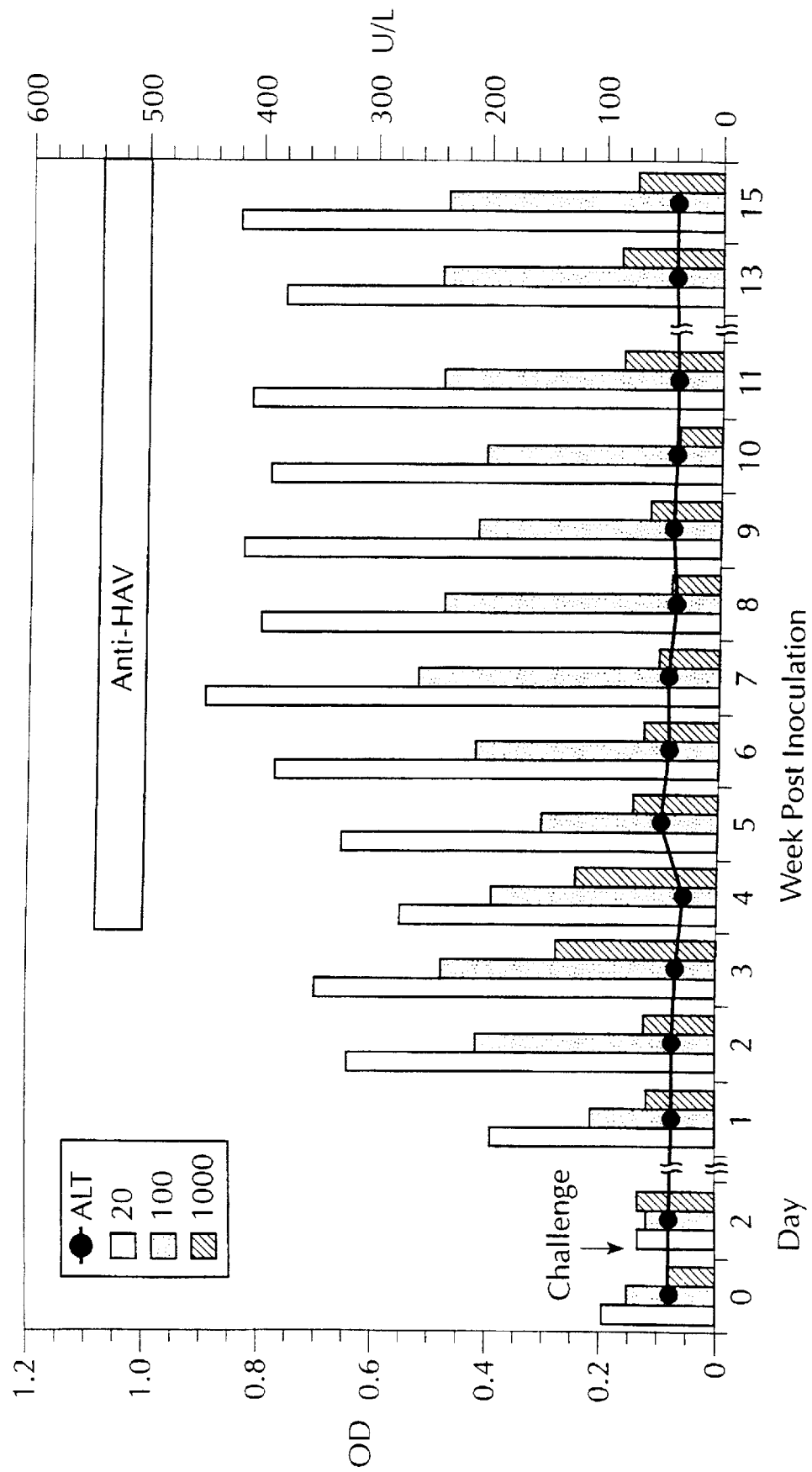
Figure 1E:
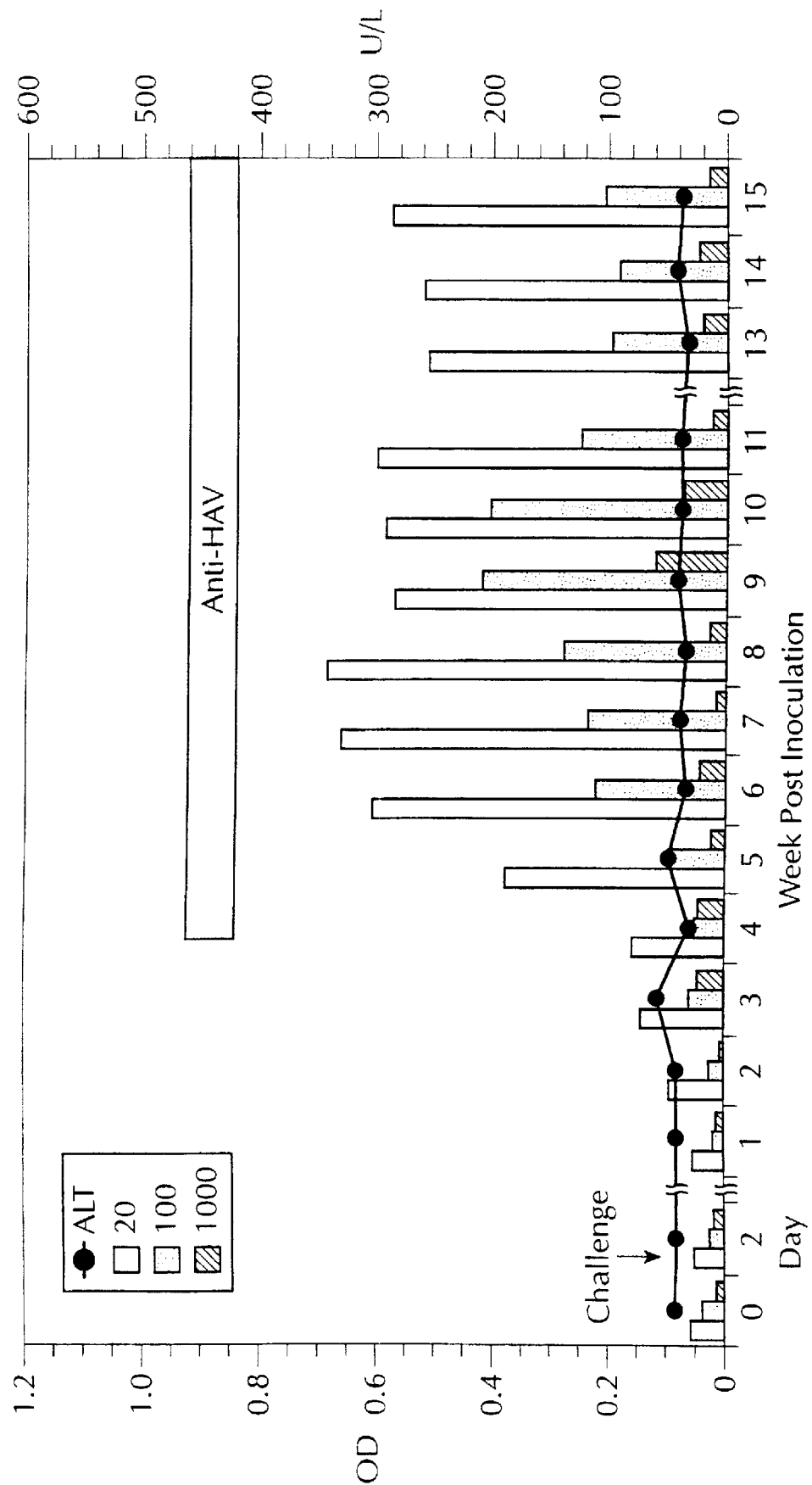
Figure 1F:
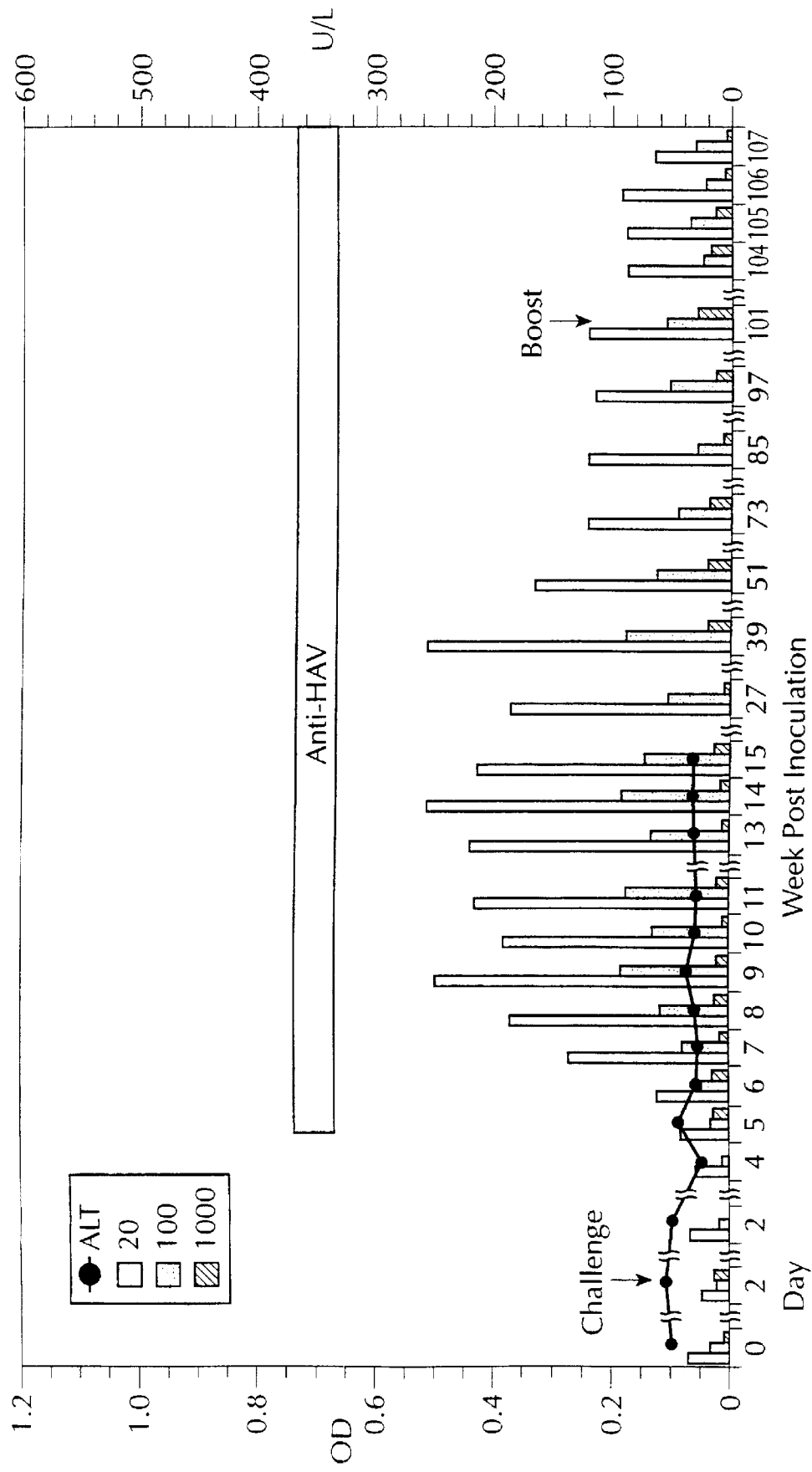

Three chimpanzees (1374, 1396, and 1420) were also inoculated with ISG and then challenged with wild-type HM-175. All three chimpanzees seroconverted to the structural proteins but did not exhibit an increase in serum ALT levels and therefore, did not develop disease (FIGS. 1D–1F). However, all three animals did develop antibodies to the proteinase. These results, indicating that viral replication had occurred in all three chimpanzees (with chimpanzees 1374 (FIG. 1F) and 1396 (FIG. 1E) both developing anti-3C titers of 1:20 while chimpanzee 1420 (FIG. 1D) reached an anti-3C titer of 1:100) were expected since injection of immune serum globulin (ISG) is known to prevent disease but not viral replication (Stapleton et al, (1995), *J. Infect. Dis.*, (Suppl. 1): S9–14).

Thus, the ability of the ELISA to confirm low levels of viral replication in three chimpanzees (1420, 1396 and 1374, see FIGS. 1D–1F) that did not exhibit signs of clinical disease suggests that the ELISA provides a useful method to detect states of limited replication in cases where the virus is not excreted in levels sufficient for detection and disease does not occur.

Finally, two chimpanzees (1332 and 1380) immunized with an inactivated HM-175 vaccine (HAVRIX) seroconverted to the structural proteins after vaccination but antibodies to the nonstructural 3C proteinase were not detected (data not shown).

These results demonstrated that the anti-3C proteinase ELISA can distinguish an individual with a natural infection from one who has been vaccinated with an inactivated HAV vaccine.

Example 2

Detection of antibodies to 3C proteinase in tamarins

To determine if the ELISA was able to detect antibodies to 3C in primates other than chimpanzees, serum from HAV infected tamarins were analyzed.

Figure 2A:
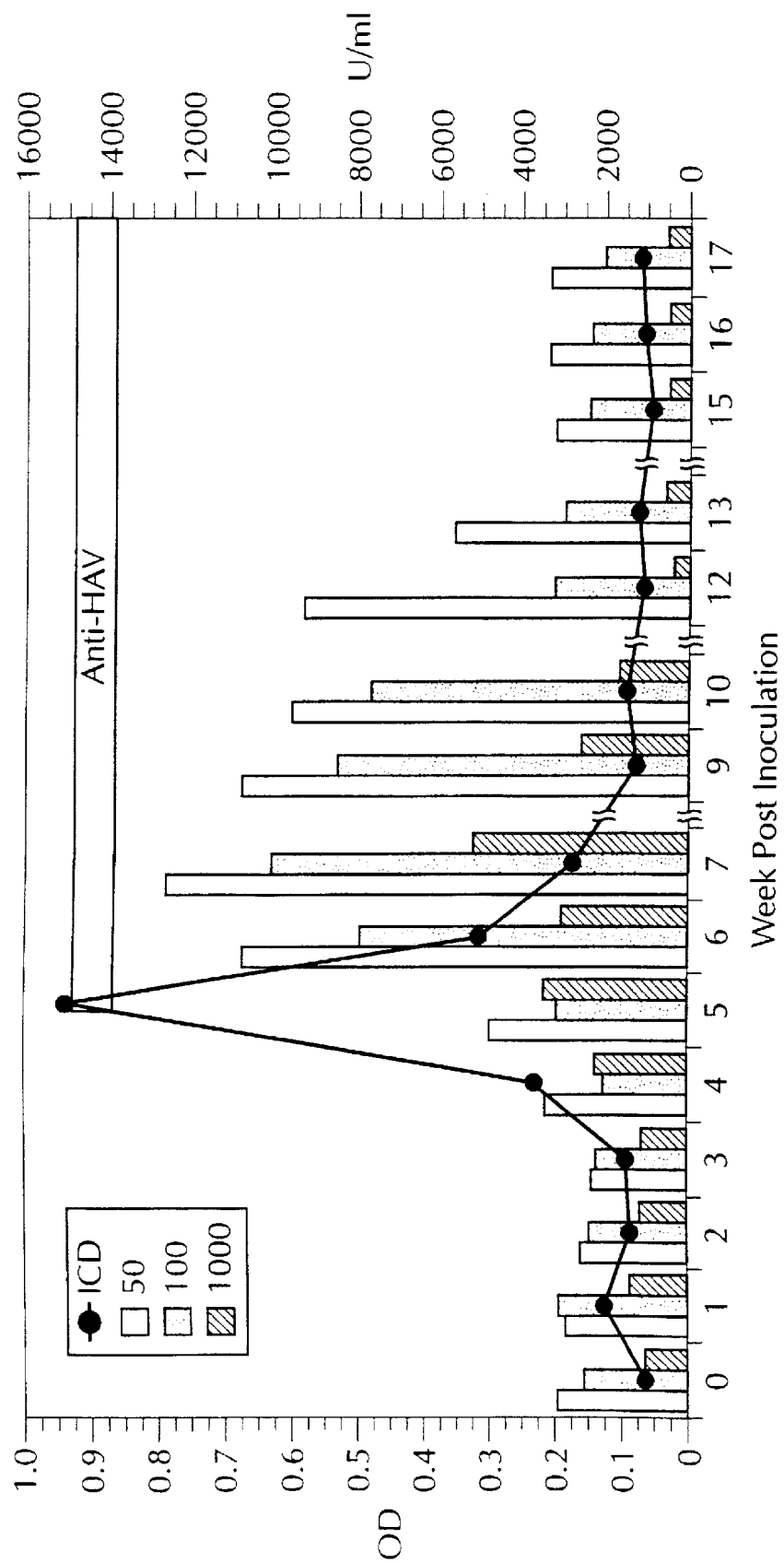
FIGS. 2A and 2B show anti-3C proteinase antibody response compared to seroconversion to the structural proteins (anti-HAV) and to isocitrate dehydrogenase (ICD) levels in tamarins infected with HAV 8Y (FIG. 2A) and HAV/7 (FIG. 2B). ICD levels are indicated as units/milliliter (U/ml) on the right-hand vertical axis of FIGS. 2A and 2B; OD levels for the anti-3C proteinase ELISA obtained using 1:50 (or 1:20), 1:100 or 1:1000 dilutions of sera are indicated in FIG. 2A as bars marked 50, 100 and 1000 respectively and in FIG. 2B as bars marked 20, 100 and 1000 respectively; and the horizontal bar labelled anti-HAV in FIGS. 2A and 2B represents samples which were seropositive for HAV structural proteins (value>2.0 for antibodies to HAV structural proteins).

Tamarin 682, infected by laparotomy and intrahepatic inoculation with a 100 ul transcription reaction of HAV cDNA clone 8Y which encodes a virus with a wild-type phenotype (Emerson et al. (1992), *J. Virol.* 66:6649–6654), exhibited a peak serum ICD level and seroconverted to the HAV structural proteins on week 5 post infection (FIG. 2A). Antibodies to 3C proteinase were first detected on week 5 post infection at low levels. However, peak antibody accumulation occurred in week 7 post infection and decreased to undetectable levels by week 15.

Figure 2B:
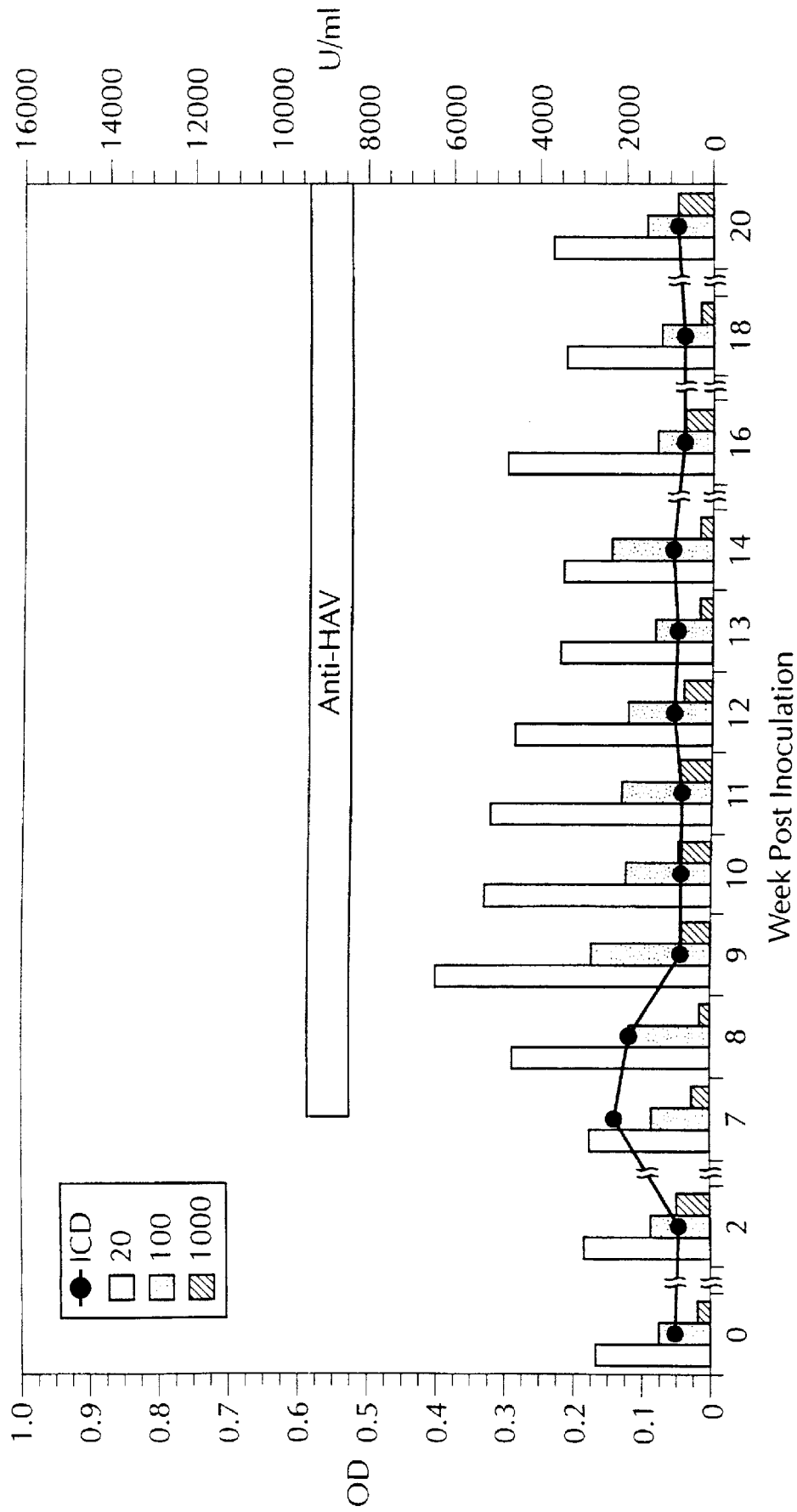

Another tamarin, 683, inoculated intravenously with $10^5$ tissue culture infectious doses of an attenuated virus, pHAV-7 (Cohen et al. (1987), *J. Virol.*, 61: 3035–3039), seroconverted to the structural proteins but serum ICD levels were much lower than those in tamarin 682 (FIG. 2B). However, this tamarin did produce anti-proteinase antibodies beginning at week 8 post infection, a week later than the peak serum ICD levels and seroconversion to structural proteins.

In sum, these data demonstrated that the anti-3C proteinase ELISA detected antibodies to the 3C proteinase in the serum of HAV infected chimpanzees in the presence or absence of overt disease and in tamarins with mild or severe hepatitis.

The data also demonstrated that the anti-proteinase antibodies were produced concurrently or immediately after the elevation in serum liver enzymes levels. In addition, the results suggested that animals that exhibited higher levels of serum liver enzymes produced higher titers of anti-proteinase antibodies.

Example 3

Detection of Anti-3C Proteinase Antibodies in Chimpanzees Using The "Further Purified 3C Proteinase"

Figure 3A:
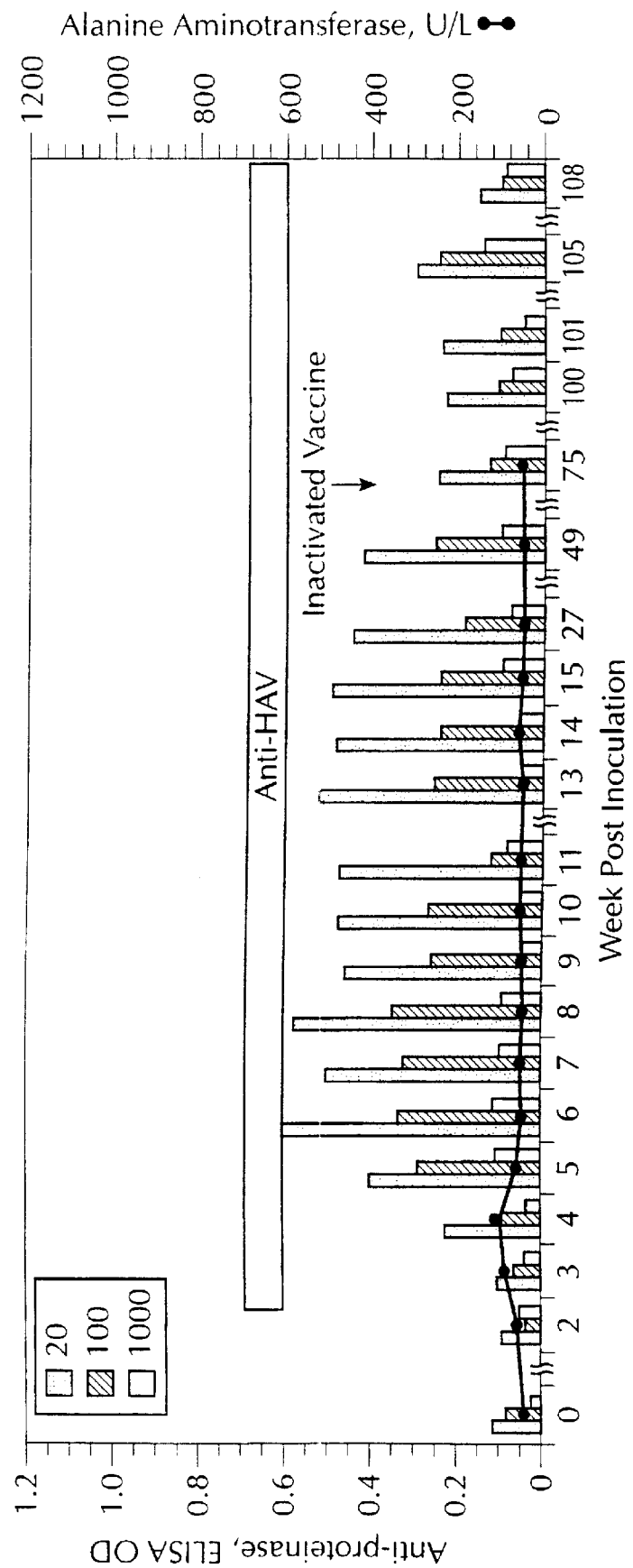
FIGS. 3A–3F show IgG antibody response to 3C proteinase in chimpanzees inoculated with virulent HAV strain HM-175 and inactivated HAV vaccine (FIG. 3A); with virulent HAV strain SD-11 (FIG. 3B); with inactivated HAV vaccine and virulent HAV strain HM-175 (FIGS. 3C and 3D); with immune serum globulin, virulent HAV strain HM-175 and inactivated HAV vaccine (FIG. 3E); and with attenuated HAV strain AGM-27 and virulent HAV, strains HM-175 and SD-11 (FIG. 3F). Antibodies to 3C proteinase and to the structural proteins (anti-HAV) were plotted, with alanine aminotransferase (ALT) levels, as a function of time relative to challenge. ALT levels are indicated as units/liter (U/L) on the right-hand vertical axis of FIGS. 3A–3F; OD levels for the anti-3C proteinase ELISA obtained using 1:20, 1:100 or 1:1000 dilutions of sera are indicated in the Figures as bars marked 20, 100 and 1000, respectively where values above the cutoff point of 0.2 for the 3C proteinase were considered positive; and the horizontal bar labelled anti-HAV in each of FIGS. 3A–3F represents samples which were seropositive for HAV structural proteins (N/S>2.0 for antibodies to HAV structural proteins).

IgG antibodies to the nonstructural 3C proteinase were detected in the sera of chimpanzee 1442 at week four (Table 1, FIG. 3A)

TABLE 1

Response of Naive or Immunized Chimpanzees to Challenge with Wild-Type HAV

| Chimpanzee | Prior immunization | Alanine aminotransferase (U/L) | | Antibody to | Antibody to 3C proteinase | | |
|---|---|---|---|---|---|---|---|
| | | Pre challenge (mean) | peak | Post challenge week | structural proteins prior to challenge | At time of challenge | 1st week detected post challenge* | Maximum titer (week) |
| 1442† | None | 48 | 103 | 4 | No | No | 4 | 1:100 (6) |
| 1300†,‡ | | 38 | 1180 | 4 | No | No | 3 | 1:1000 (5) |
| 1373§ | | 40 | 187 | 7 | No | No | 8 | 1:100 (9) |
| 1451§ | | 56 | 527 | 5 | No | No | 6 | 1:1000 (6) |
| 1309¶ | Attenuated | 28 | 32 | 11 | Yes | No | ND | ND |
| 1333¶ | vaccine■ | 33 | 41 | 7 | Yes | No | ND | ND |
| 88AO2** | | 45 | 47 | 12 | Yes | No | 1‡‡ | 1:20 (1)‡‡ |
| 88AO4** | | 75 | 83 | 3 | Yes | No | 1††2‡‡ | 1:20 (1) ‡(, 1:20 (2)‡‡ |
| 1332¶ | Inactivated | 37 | 40 | 2 | Yes | No | ND | ND |
| 1380¶ | vaccine■ | 42 | 47 | 2 | Yes | No | 1 | 1:20 (1) |
| 1374 | Immune | 46 | 51 | 2 | No■ ■ | No | 7 | 1:100 (10) |

TABLE 1-continued

Response of Naive or Immunized Chimpanzees to Challenge with Wild-Type HAV

| | | Alanine aminotransferase (U/L) | | | Antibody to structural proteins prior to challenge | Antibody to 3C proteinase | | |
|---|---|---|---|---|---|---|---|---|
| Chimpanzee | Prior immunization | Pre challenge (mean) | peak | Post challenge week | | At time of challenge | 1st week detected post challenge* | Maximum titer (week) |
| 1396 | globulin | 45 | 49 | 3 | No■■ | No | 5 | 1:100 (6) |
| 1420 | (ISG)■■ | 38 | 48 | 5 | No■■ | No | 5 | 1:100 (6) |

*= First week antibodies to 3C proteinase detected following challenge (week 0) with wild-type virus
†= Inoculated with wild-type HM-175 strain
‡= Previously inoculated with attenuated virus but not infected
§= Inoculated with wild-type SD-11 strain
■ = Chimpanzees vaccinated prior to challenge with wild-type virus
¶= Vaccinated with attenuated or inactivated strain of HM-175
**= Inoculated with HAV strain AGM-27
††= First week antibodies to 3C proteinase detected following challenge with HM-175 strain (1st challenge)
‡‡= First week antibodies to 3C proteinase detected following challenge with SD-11 strain (2nd challenge)
§§= Chimpanzees inoculated with immune globulin (human) prior to challenge with wild-type virus
■■ = Present but not detectable by standard assays
ND = None detected post inoculation and the antibodies to the 3C proteinase were detected through week 105 post-inoculation, after which time they decreased below the level of detection. Further, IgM antibodies to 3C proteinase peaked at week 4 post-inoculation but declined rapidly to undetectable levels by week 6 post-inoculation (FIG. 4). Chimpanzee 1300, which was also infected with wild-type HM-175, seroconverted to the structural proteins and produced peak enzyme levels at weeks 3 and 4 respectively post-inoculation. Antibodies to 3C proteinase were also detected at week three post-inoculation and reached a peak titer of 1:1000 by week 5 (Table 1).

Figure 3B:
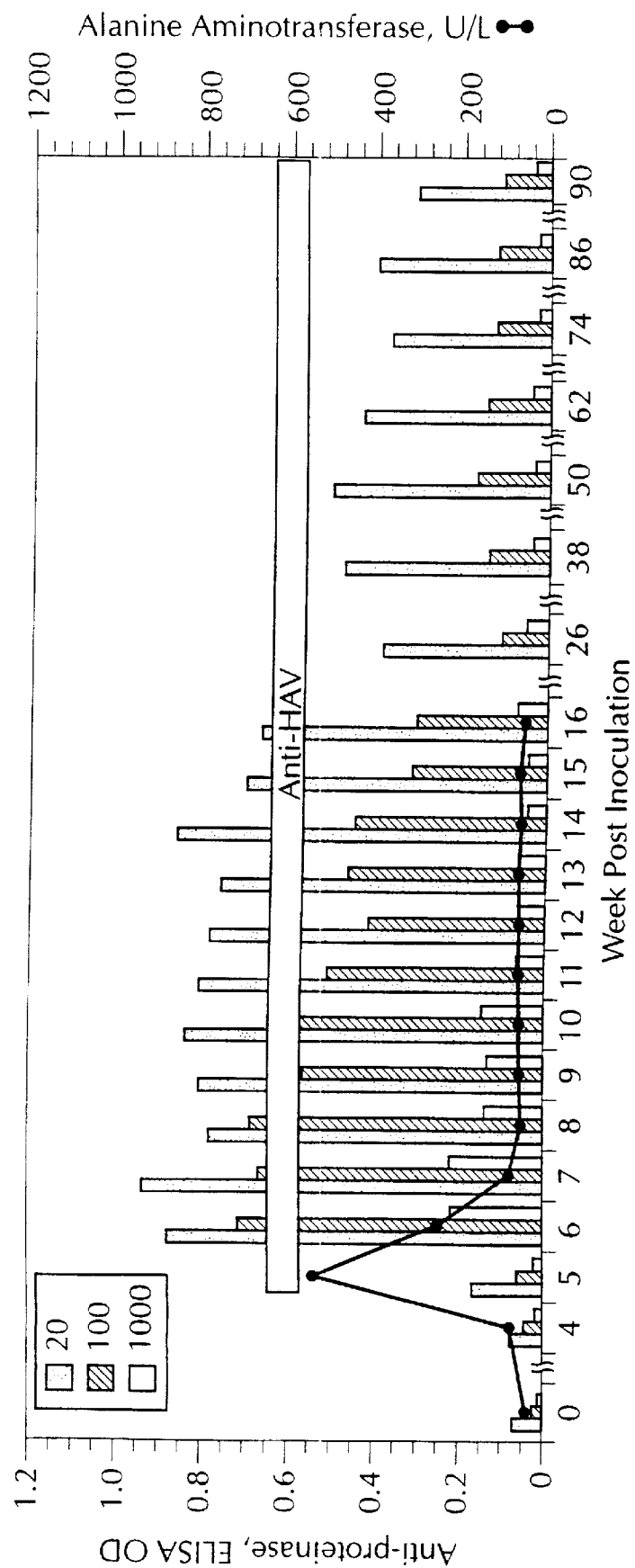

As observed before with the "purified 3C proteinase" ELISA (see Example 1), the "further purified 3C proteinase" ELISA detected antibodies to the proteinase in the SD-11 infected chimpanzees 1373 (Table 1) and 1451 (Table 1, FIG. 3B). Chimpanzee 1373 produced detectable levels of anti-proteinase on week 8 post inoculation, one week after seroconversion to structural proteins and peak enzyme production. Chimpanzee 1451, which produced significantly higher levels of anti-3C proteinase than chimpanzee 1373, seroconverted to 3C proteinase on week six post-inoculation, one week after seroconversion to structural proteins.

Figure 3C:
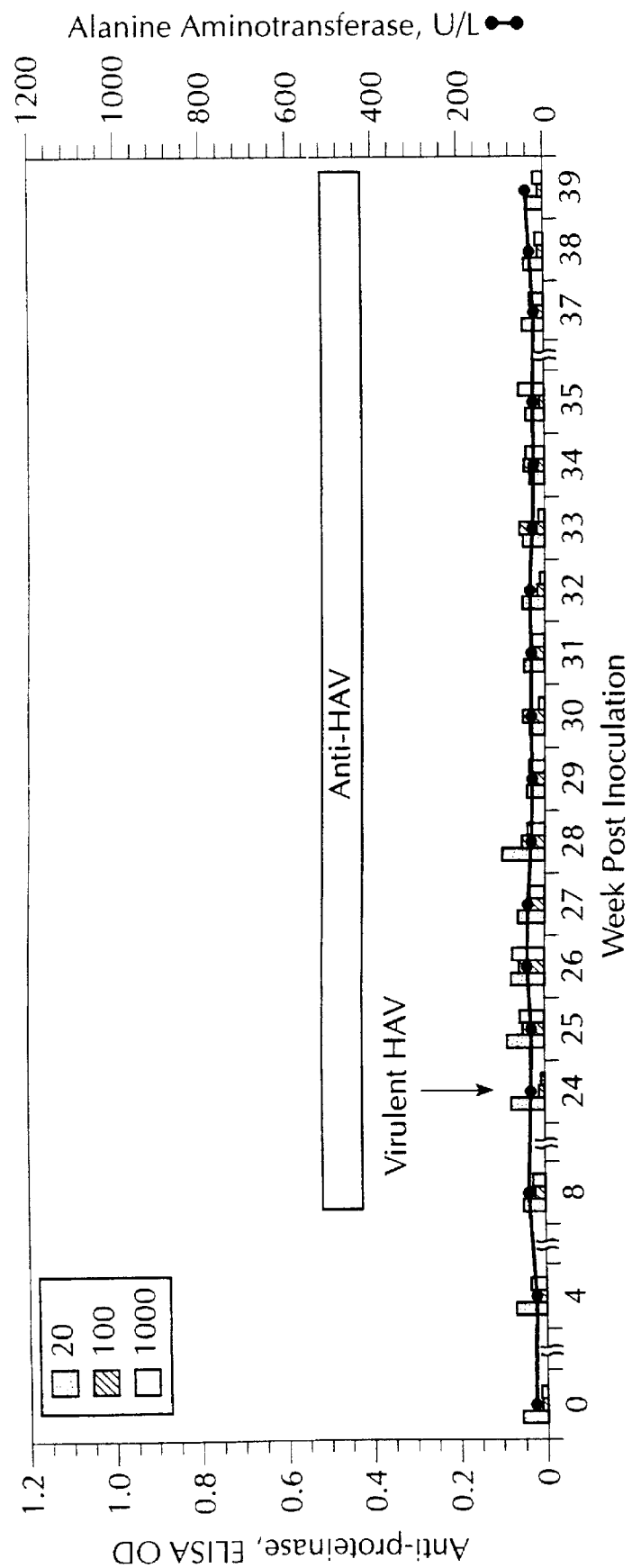
Figure 3D:
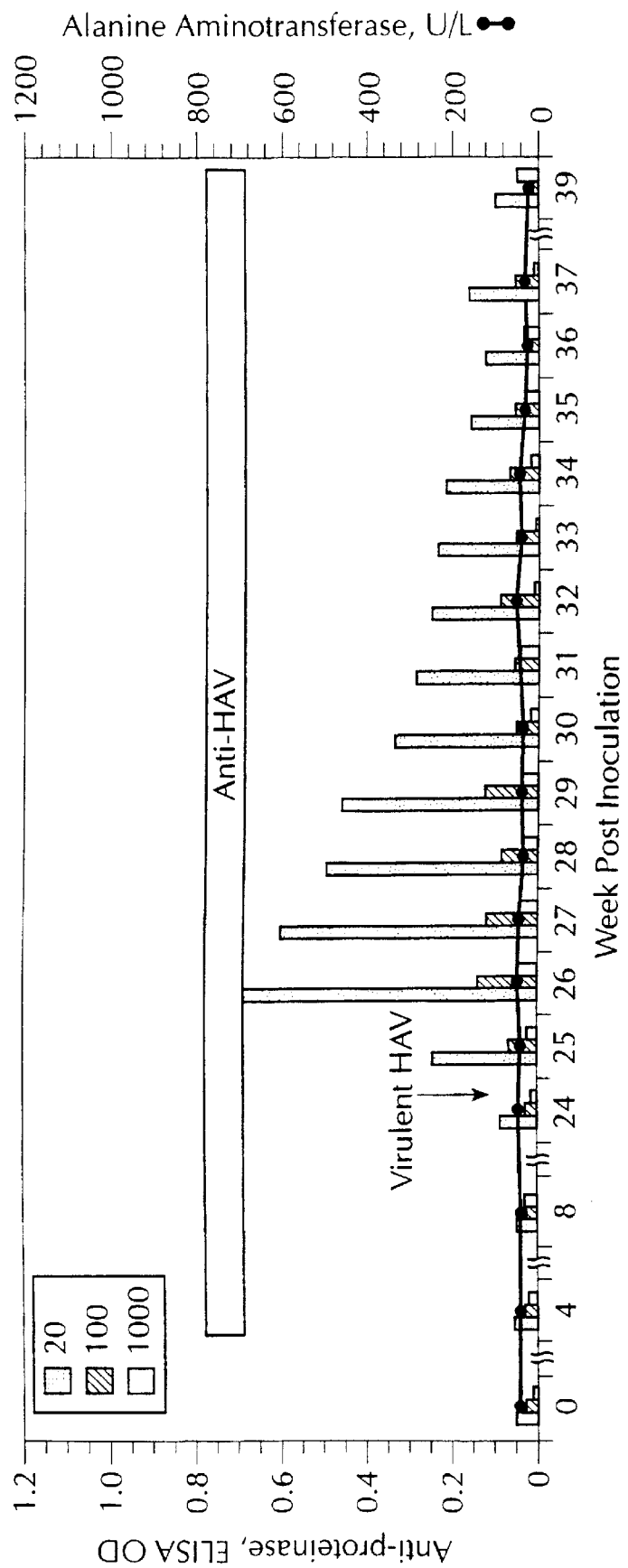

The sera of two chimpanzees vaccinated with an inactivated HM-175 vaccine (1332 and 1380) were also analyzed using the "further purified 3C proteinase" ELISA. These chimpanzees seroconverted to the structural proteins after vaccination and did not exhibit elevated serum liver enzyme levels following immunization or after challenge with virulent HM-175 (Table 1). Antibodies to the nonstructural proteinase 3C were not detected in chimpanzee 1332 (FIG. 3C, Table 1) either before or after challenge with HM-175, indicating that the vaccination with the inactivated vaccine in this case protected against significant replication of the virus. However, chimpanzee 1380, which also remained anti-3C negative after vaccination with inactivated vaccine, (FIG. 3D) did exhibit anti-3C reactivity after challenge with HM-175. Therefore in this animal, vaccination provided protection against hepatitis but not against infection since replication of the challenge virus occurred as indicated by the detection of anti-3C proteinase antibodies after challenge with wild-type HM-175. Thus, since there was no increase in serum ALT levels in chimp 1380 after challenge (FIG. 3D) and PCR analyses of fecal samples were negative for viral excretion (data not shown), the antibodies to 3C proteinase were the only indicator that replication of the virus had occurred.

Chimpanzees 1309 and 1333, vaccinated with an attenuated vaccine, produced antibodies to the structural proteins and mounted a fully protective immune response since they did not develop hepatitis or become infected after challenge (Table 1). In addition, neither animal produced antibody to 3C after vaccination or challenge, suggesting that the attenuated virus was able to stimulate production of antibodies to the structural protein even though replication of the vaccine virus was insufficient to stimulate anti-3C antibodies. Thus, inoculation with an attenuated HAV vaccine can result in limited viral replication and seroconversion to the structural proteins in the absence of an antibody response to the 3C proteinase.

Figure 3E:
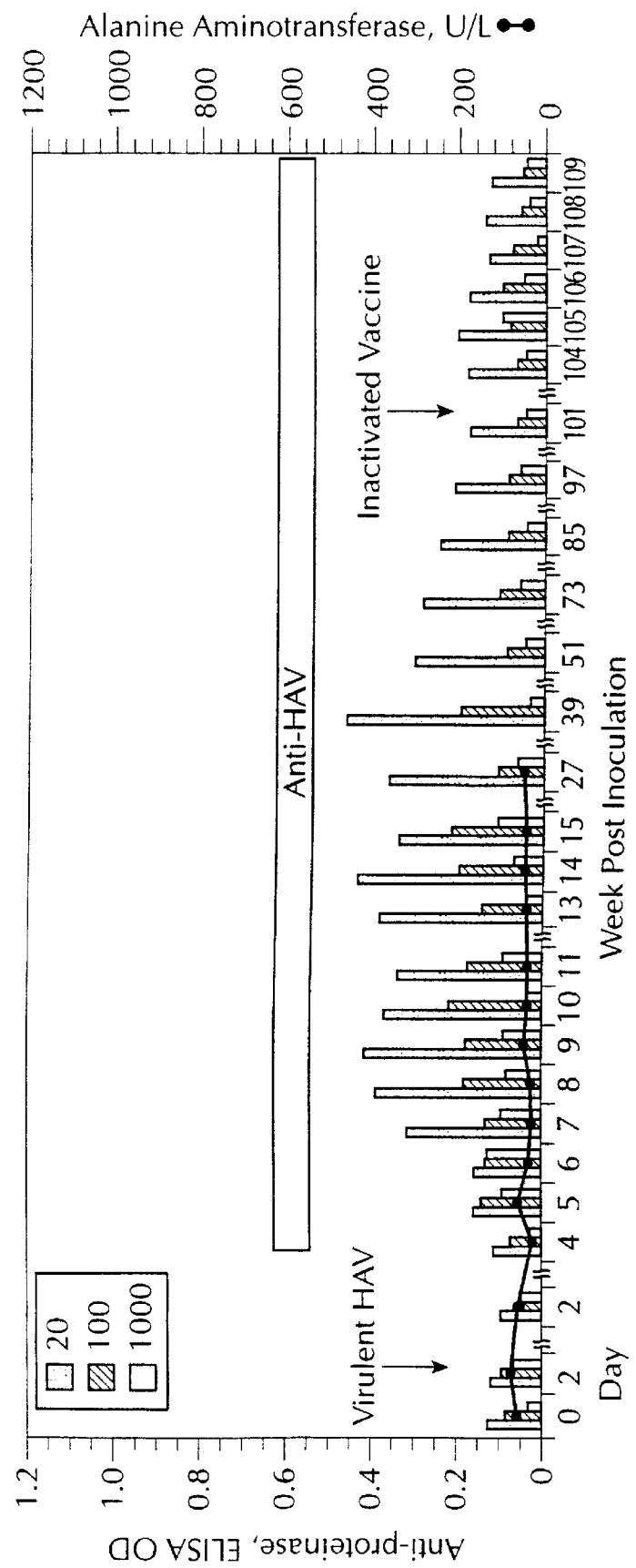

The three chimpanzees (1374, 1396, and 1420) (Table 1, FIG. 3E) that were inoculated with ISG and then challenged with wild-type HM-175 developed anti-3C titers of 1:100, indicating that viral replication had occurred. Thus, the ELISA was able to confirm low levels of viral replication in three passively immunized chimps that did not exhibit clinical disease. Subsequent intramuscular immunization of chimp 1374 with inactivated HAV vaccine (1.0 ml of the SmithKline Beecham HAVRIX vaccine) boosted antibodies to the structural proteins but did not increase the anti-3C antibody titer (FIG. 3E).

Figure 3F:
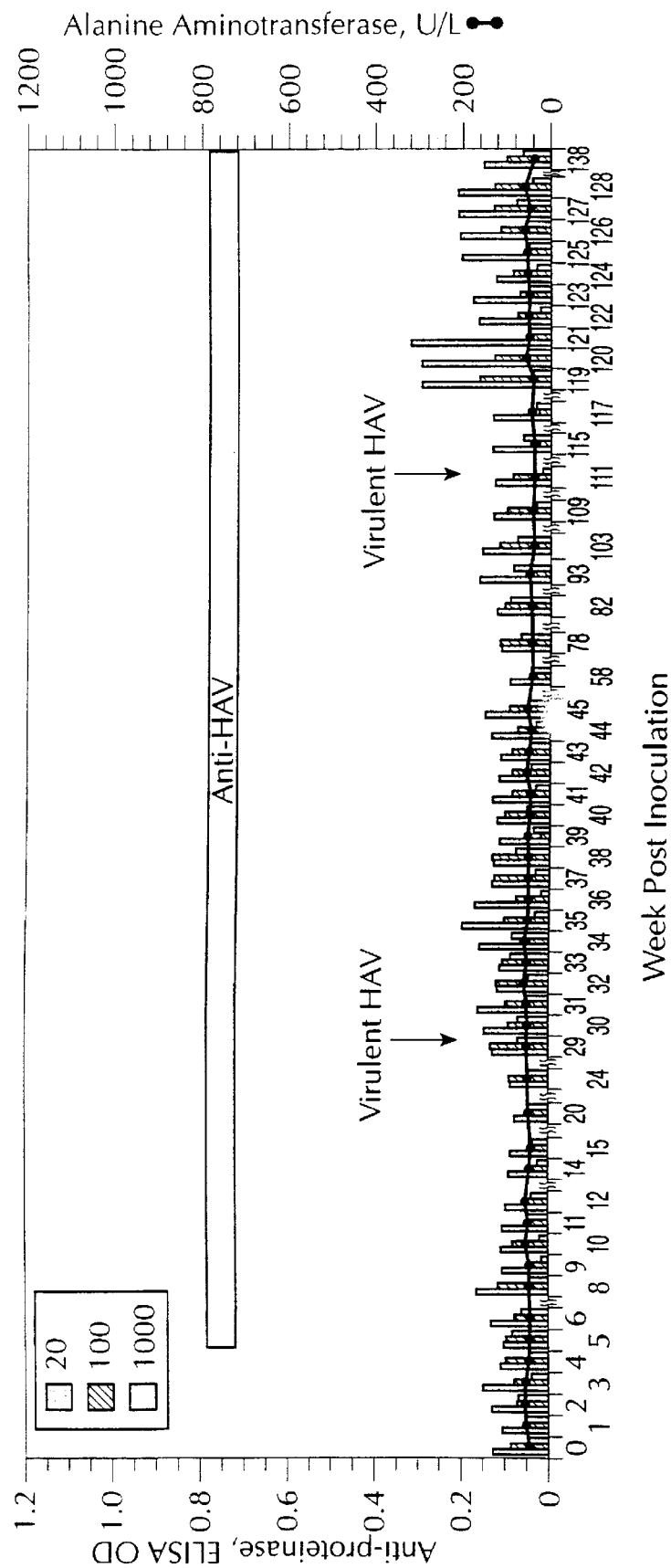

Infection of chimpanzees 88A02 (FIG. 3F) and 88A04 (Table 1) with the simian strain of HAV, AGM-27 was associated with a low level of virus replication (Emerson, S. U. et al. (1996) *J. Infect. Dis.*, 173:592–597) and caused seroconversion to HAV structural proteins in the absence of hepatitis. Although the AGM-27 virus did replicate, albeit to a low level in both animals, only chimpanzee 88A04 transiently displayed detectable levels of anti-3C (titer of 1:20) three months after inoculation with AGM-27 (data not shown).

Following the AGM-27 infection, the chimpanzees 88A02 and 88A04 were challenged first with wild-type HM-175 and later with SD-11. Neither chimpanzee developed hepatitis A as indicated by stable ALT levels. However, there did appear to be a boost in antibodies to 3C after the SD-11 challenge in chimpanzee 88A02 (FIG. 3F) and after both the HM-175 challenge and SD-11 challenge in chimpanzee 88A04 (data not shown), indicating low level replication of the viruses and therefore demonstrating that seroconversion to structural proteins did not necessarily prevent infection. In addition, the ability to detect antibodies to 3C proteinase in chimps 88A04 abd 88A02 provided further evidence of the versatility of this assay as the assay has now been demonstrated to recognize antibodies elicited by three different HAV strains, HM-175, SD-11 and AGM-27.

Example 4

Detection of Anti-3C proteinase antibodies in tamarins using The "Further Purified 3C Proteinase"

Figure 5A:
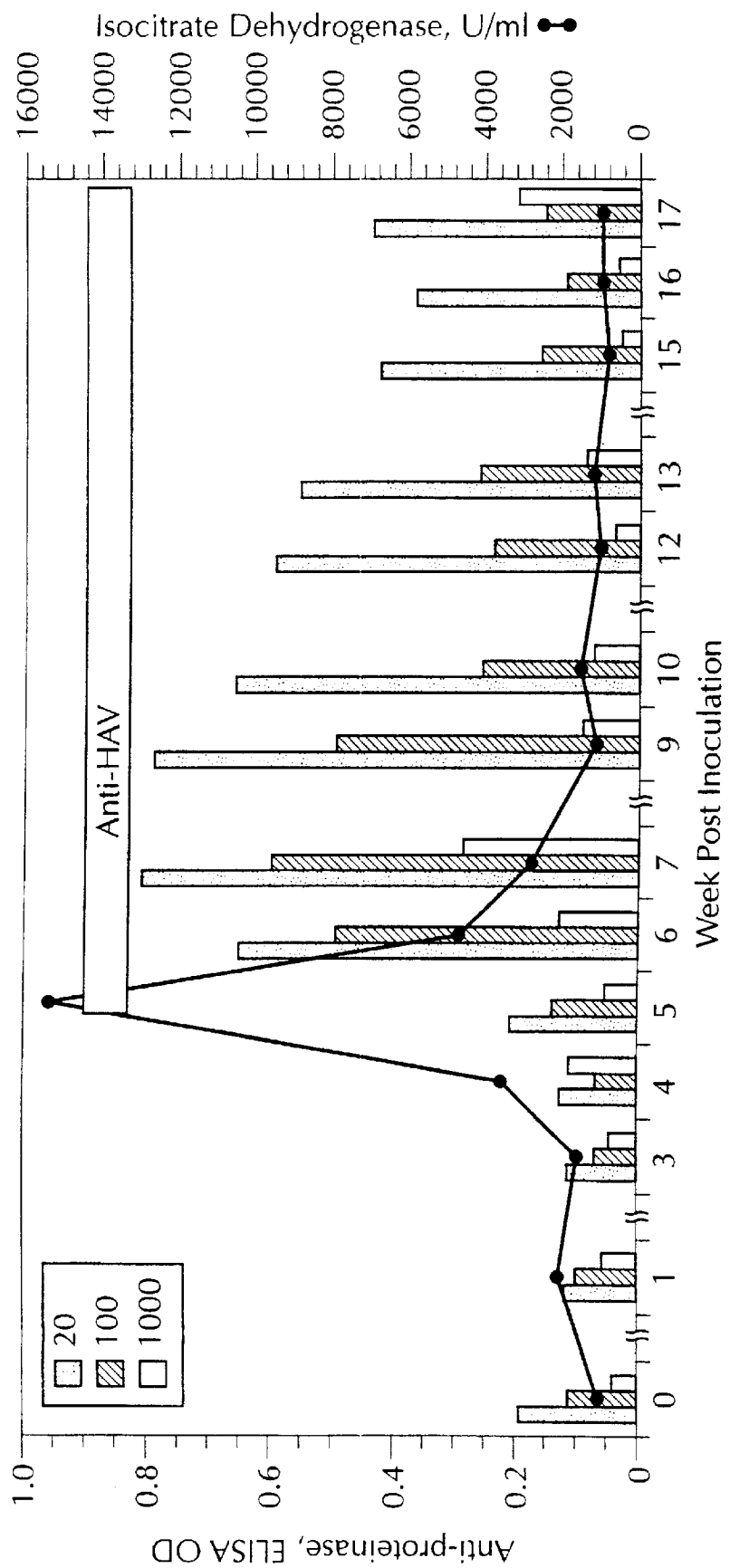
FIGS. 5A and 5B show antibody response to 3C proteinase in tamarins infected with virulent HAV strain HM-175 (8Y) (FIG. 5A) or with attenuated HAV strain HM-175 (HAV/7) (FIG. 5B). Antibodies to 3C proteinase and to the structural proteins (anti-HAV) were plotted with isocitrate dehydrogenase (ICD) levels, as a function of time relative to challenge. IcD levels are indicated as units/milliliter (u/ml) on the right-hand vertical axis of FIGS. 5A and 5B; OD levels for the anti-3C proteinase ELISA obtained using 1:20, 1:100 or 1:1000 dilutions of sera are indicated in FIGS. 5A and 5B as bars marked 20, 100 and 1000, respectively; where values above the cutoff point of 0.2 for the 3C proteinase were considered positive; and the horizontal bar labelled anti-HAV in each of FIGS. 5A and 5B represents samples which were seropositive for HAV structural proteins (N/S>2.0 for antibodies to HAV structural proteins).

The "further purified 3C proteinase" ELISA was also used to analyze serum from HAV-infected tamarins. Antibodies to 3C proteinase in tamarin 682 (infected by transfection with a virulent HAV encoded by the HAV cDNA clone (8Y)) were first detected at week 6 post-inoculation (FIG. 5A), peaked during week 7 and were still detectable at week 17 post-inoculation.

Figure 5B:
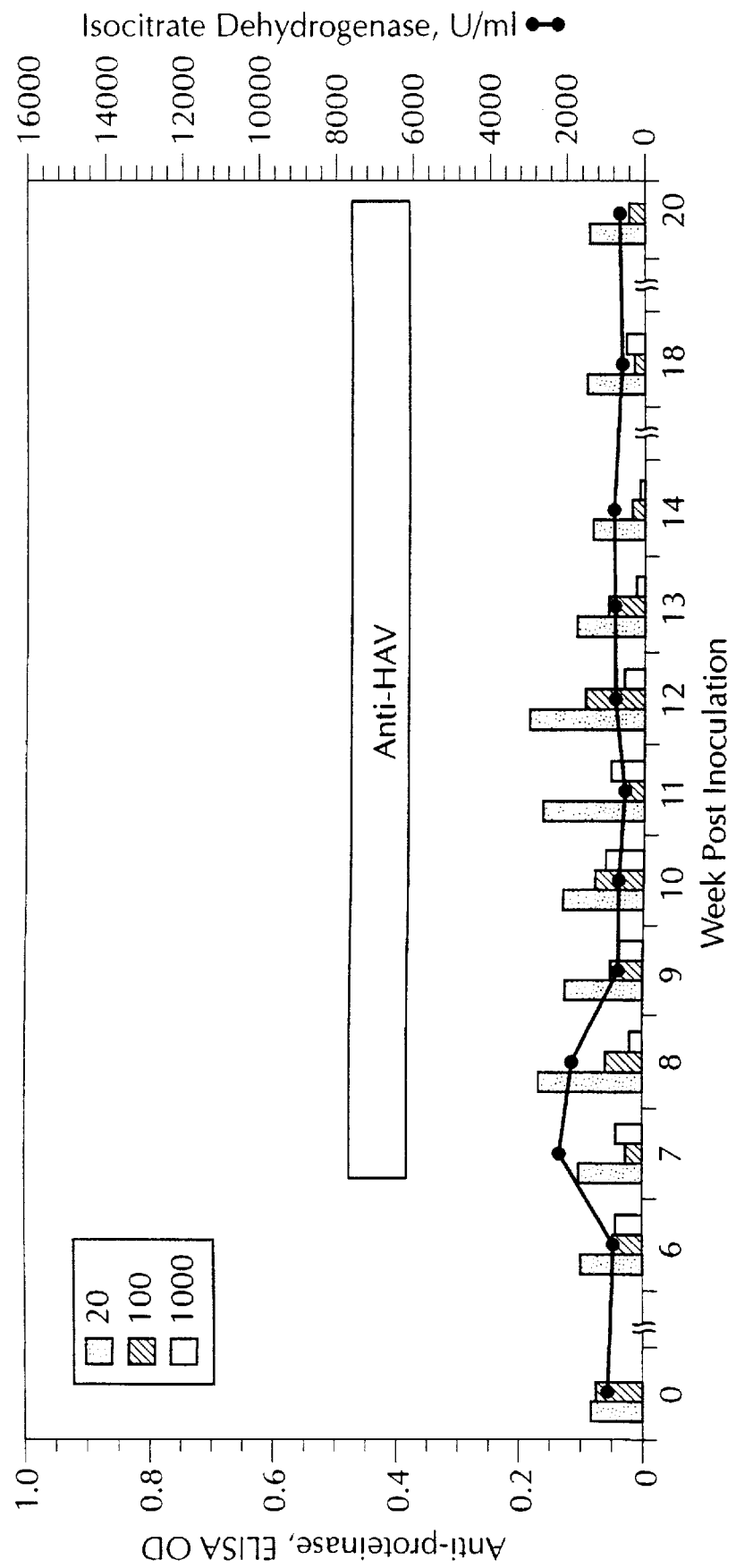

By comparison, antibodies to the 3C proteinase did not reach significant levels in tamarin 683 (FIG. 5B) (inoculated with an attenuated strain of HM-175), even though there were indications of viral replication such as fecal viral shedding as measured by Southern blot analysis (data not shown).

In sum, the data presented above indicate that an assay utilizing HAV 3C proteinase as the antigen can accurately detect antibodies to the nonstructural 3C proteinase of HAV and therefore distinguish an immune response to active infection by HAV from an immune response resulting from vaccination with an inactivated HAV vaccine. In addition, an assay utilizing HAV 3C proteinase as the antigen provides a useful and simple method for the detection of limited replication in cases where virus is not excreted to detectable levels and disease does not occur.

What is claimed is:

1. A method for determining whether a subject has been vaccinated against hepatitis A virus or naturally infected with hepatitis A virus, said method comprising:

(a) contacting a biological sample from said subject with HAV structural proteins under conditions which permit the formation of a complex between antibodies to the structural proteins and the structural proteins; and (b) contacting a sample which forms a complex in step (a) with HAV 3C proteinase under conditions which permit the formation of a complex between antibodies to the 3C proteinase and the 3C proteinase, wherein the detection of a complex between the antibodies to 3C proteinase and the 3C proteinase indicates that said subject has been naturally infected with hepatitis A virus and a failure to detect said complex indicates that the subject has been vaccinated against hepatitis A virus.

2. The method of claim 1, wherein the 3C proteinase in step (b) is bound to a solid support.

3. The method of claim 2, wherein the biological sample is contacted in step (b) with a recombinantly expressed 3C proteinase.

4. The method of claim 3, wherein the antibody-proteinase complex in step (b) is detected using a labelled secondary antibody.

5. The method of claim 4, wherein the antibodies detected in step (b) are IgG antibodies.

6. The method of claim 4, wherein the antibodies detected in step (b) are IgM antibodies.

7. The method of claim 1, wherein the presence of antibodies to 3C proteinase is detected in step (b) by measuring the 3C proteinase activity of the 3C proteinase contacted with the biological sample, an inhibition of 3C proteinase activity as compared to the 3C proteinase activity of 3C proteinase not contacted with the biological sample indicating the presence of antibodies to 3C proteinase in the biological sample.

8. The method of claim 7, wherein the 3C proteinase activity is determined by incubating the 3C proteinase with at least one 3C proteinase substrate.

9. The method of claim 8, wherein the 3C proteinase substrate is labelled.

10. A method for determining whether a subject has been infected with hepatitis A virus; said method comprising contacting a biological sample from said subject with HAV 3C proteinase under conditions which permit the formation of a complex between antibodies to the 3C proteinase and the 3C proteinase, wherein the detection of a complex between the antibodies to 3C proteinase and the 3C proteinase indicates that said subject has been naturally infected with HAV.

11. The method of claim 10, wherein the 3C proteinase is bound to a solid support.

12. The method of claim 11, wherein the biological sample is contacted with a recombinantly expressed 3C proteinase.

13. The method of claim 12, wherein the antibody-proteinase complex is detected using a labelled secondary antibody.

14. The method of claim 13, wherein the antibodies detected are IgG antibodies.

15. The method of claim 13, wherein the antibodies detected are IgM antibodies.

16. The method of claim 10, wherein the presence of antibodies to 3C proteinase is detected by measuring the 3C proteinase activity of the 3C proteinase contacted with the biological sample, an inhibition of 3C proteinase activity as compared to the 3C proteinase activity of 3C proteinase not contacted with the biological sample indicating the presence of antibodies to 3C proteinase in the biological sample.

17. The method of claim wherein the 3C proteinase activity is determined by incubating the 3C proteinase with at least one 3C proteinase substrate.

18. The method of claim 17, wherein the 3C proteinase substrate is labelled.

19. A method for determining whether a subject seropositive for antibodies to hepatitis A virus structural proteins is seropositive as a result of infection with hepatitis A virus or of vaccination against hepatitis A virus, said method comprising contacting a biological sample from said patient with HAV 3C proteinase under conditions which permit the formation of a complex between antibodies to 3C proteinase and the 3C proteinase, wherein the detection of a complex between the antibodies to 3C proteinase and the 3C proteinase indicates that said subject has been naturally infected with hepatitis A virus and a failure to detect said complex indicates that the individual has been vaccinated against hepatitis A virus.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 7 amino acids
      (B) TYPE: amino acid
      (C) STRANDEDNESS: unknown
      (D) TOPOLOGY: unknown (ii) SEQUENCE DESCRIPTION: SEQ ID NO:1:

Glu Leu Arg Thr Gln Phe Ser
1             5